US006833379B2

(12) United States Patent
Filić et al.

(10) Patent No.: US 6,833,379 B2
(45) Date of Patent: Dec. 21, 2004

(54) CRYSTAL MODIFICATION OF TORASEMIDE

(75) Inventors: Darko Filić, Zagreb (HR); Miljenko Dumić, Zagreb (HR); Aleksandar Danilovski, Rijeka (HR); Božena Klepić, Jastrebarsko (HR); Ines Fistrić, Zagreb (HR); Marina Orešić, Sesvete (HR); Jasna Horvat Mikulčić, Zagreb (HR)

(73) Assignee: Pliva Hrvatska d.o.o. (HR)

( * ) Notice: Subject to any disclaimer, the term of this patent is extended or adjusted under 35 U.S.C. 154(b) by 0 days.

(21) Appl. No.: 10/096,277

(22) Filed: Mar. 13, 2002

(65) Prior Publication Data

US 2003/0055258 A2 Mar. 20, 2003

Related U.S. Application Data

(63) Continuation of application No. 09/434,439, filed on Nov. 5, 1999, now Pat. No. 6,399,637, which is a continuation of application No. 09/187,046, filed on Nov. 6, 1998, now abandoned.

(30) Foreign Application Priority Data

Oct. 2, 1998 (HR) .......................................... P980532A

(51) Int. Cl.[7] ...................... A61K 31/47; C07D 213/62; C07D 213/71
(52) U.S. Cl. ........................ 514/347; 546/294; 514/347
(58) Field of Search .......................... 514/347; 546/294, 546/291

(56) References Cited

U.S. PATENT DOCUMENTS

| 4,018,929 A | 4/1977 | Delarge et al. ............. 514/347 |
| 4,055,650 A | 10/1977 | Delarge et al. ............. 514/347 |
| RE30,633 E | 6/1981 | Delarge et al. ............. 514/347 |
| 4,473,693 A | 9/1984 | Topfmeier et al. |
| RE34,580 E | 4/1994 | Topfmeier et al. .......... 546/291 |
| RE34,672 E | 7/1994 | Topfmeier et al. .......... 514/347 |
| 5,914,336 A * | 6/1999 | Dreckmann-Behrendt ... 514/37 |
| 6,166,045 A * | 12/2000 | Dreckmann-Behrendt et al. ........................... 514/37 |

FOREIGN PATENT DOCUMENTS

| EP | 0212537 | 8/1986 | ................. 514/347 |
| EP | 0212537 B1 | 1/1990 | |

OTHER PUBLICATIONS

P.L. Dupont, et al. Structure Cristalline et Moléculaire d'un Diurétique Dërivë de l'Alkyl–1 [(Phénylamino–pyridyl–3)sulfonyl]–3 Urée: la Torasémide ($C_{15}H_{20}N_4SO_3$ ) Acta Cryst. B34:1304–1310 (1978).

Rollinger, J.M., et al., Crystal forms of torasemide: new insights, European Journal of Pharmaceutics and Biopharmaceutics, 53 (2002) 75–86.

Rollinger, J.M. et al., "Crystal Forms of Torasemide: New Insights," European Journal of Pharmaceutics and Biopharmaceutics, 53 (2002) pp. 75–86.

Masereel, B. et al., "Synthesis and Pharmacology of pyrid–3–ylsulfonylcyanogyanidines as Diuretics," European Journal of Medicinal Chemistry, vol. 30, No. 4, Apr. 1995 (Apr. 1995), pp. 343–351.

(List continued on next page.)

Primary Examiner—Rita Desai
Assistant Examiner—Janet Coppins
(74) Attorney, Agent, or Firm—Finnegan, Henderson, Farabow, Garrett & Dunner, L.L.P.

(57) ABSTRACT

The present invention relates to the characterization of a new crystal modification III of torasemide, to a process for the preparation thereof by the use of controlled acidifying of alkaline solutions of torasemide with inorganic or organic acids with or without addition of a crystal seed, to its use as a raw material for the preparation of the crystal modification I of torasemide and of pharmaceutically acceptable salts of torasemide as well as to pharmaceutical forms containing this new crystal modification III of torasemide.

27 Claims, 1 Drawing Sheet

DISSOLUTION TEST OF TORASEMIDE IN WATER (USP 23)
(37°C, 50 rpm, 1000 ml)

◆ MODIFICATION I ■ MODIFICATION II ▲ MODIFICATION III

OTHER PUBLICATIONS

Dupont, L. et al., "Structure d'une second variete de la torassemide" Acta Crystallographica, Sec. B, vol. B34, No. 8, Aug. 1978 (Aug. 1978), pp. 2659–2662.

Declaration under 37 C.F.R. §1.132 of Fritz Topfmeier (Dec. 14, 1987), in U.S. Application No. 896,355, now U.S. Patent No. 4,743,693.

Kondo, N. et al. "Chemical structure of physico–chemical properties of torasemide," Iyakuhin Kenkyu, vol. 25, No. 9, Sep. 1994 (Sep. 1994), pp. 734–750.

Danilovski, A. et al. "Chemistry of Torasemide, Molecular and Crystal Structure fo New Polymorph N" CCACAA 74 (1) 103–120 (2001).

Written Opinion, PCT/HP99/00023 (Jun. 16, 2000) (6 pages).

Applicant's Reply to Written Opinion, PCT/HR99/0023 (Feb. 10, 2000) (11 pages).

Third Party Observations in respect of EP 99949272.1 arising from WO 00/20395 (Jun. 26, 2002) (6 pages).

Applicant's Statement in Response to the "Third Party Observations in respect of EP 99949272.1 arising from WO 00/29395" (Jul. 24, 2003) (11 pages).

* cited by examiner

US 6,833,379 B2

CRYSTAL MODIFICATION OF TORASEMIDE

This is a continuation of Application Ser. No. 09/434,439, filed Nov. 5, 1999, now U.S. Pat. No. 6,399,637, which is a continuation of application Ser. No. 09/187,046 filed Nov. 6, 1998, now abandoned, the contents of which are incorporated herein by reference.

TECHNICAL FIELD

The present invention relates to a new crystal modification of N-(1-methylethyl aminocarbonyl)-4-(3-methylphenylamino)-3-pyridinesulfonamide (in the further text of the application designated by its generic name "torasemide"), particularly to a new crystal modification III of torasemide, to processes for its preparation, to its use as a raw material for the preparation of the crystal modification I of torasemide and of pharmaceutically acceptable salts of torasemide as well as to pharmaceutical forms containing the said new modification III of torasemide as the active ingredient.

BACKGROUND OF INVENTION

Torasemide is a compound with interesting pharmacological properties, which is described in DE patent 25 16 025 (Example 71). As a diuretic of Henle's loop it is useful as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, decreasing of intraocular pressure, acute or chronic bronchitis, in the treatment of cerebral edema caused by trauma, ischemia, concussion of the brain, metastases or epileptic attacks and in the treatment of nasal infections caused by allergens.

The ability of a substance to exist in more than one crystal form is defined as polymorphism and these different crystal forms are named "polymorph modifications" or "polymorphs". In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. Polymorphism is found in several organic compounds. Among medicaments polymorphism is found in about 70% of barbiturates, 60% of sulfonamides and 60% of steroids and about 50% of medicaments of the said classes are not present on the market in their most stable forms (T. Laird, Chemical Development and Scale-up in the Fine Chemical Industry, Principles and Practices, Course Manual, Scientific Update, Wyvem Cottage, 1996).

The different polymorphs of a substance possess different energies of the crystal lattice and, thus, in solid state they show different physical properties such as form, density, melting point, colour, stability, dissolution rate, milling facility, granulation, compacting etc., which in medicaments may affect the possibility of the preparation of pharmaceutical forms, their stability, dissolution and bioavailability and, consequently, their action.

Polymorphism of medicaments is the object of studies of interdisciplinary expert teams [J. Haleblian, W. McCrone, *J. Pharm. Sci.* 58 (1969) 911; L. Borka, *Pharm. Acta Helv.* 66 (1991) 16; M. Kuhnert-Brandstätter, *Pharmazie* 51 (1996) 443; H. G. Brittain, *J. Pharm. Sci.* 86 (1997) 405; W. H. Streng, DDT 2 (1997) 415; K. Yoshii, *Chem. Pharm. Bull.* 45 (1997) 338, etc.] since a good knowledge of polymorphism represents a precondition for a critical observation of the whole process of medicament development. Thus, at deciding on the production of a pharmaceutical form in solid state and with regard to the dose size, stability, dissolution and anticipated action, it is necessary to determine the existence of all solid state forms (on the market some computer programmes can be found, e.g. >>Polymorph<< as a module of >>Cerius2<< programme, MSI Inc., USA) and to determine the stability, dissolution and thermodynamic properties of each of them. Only on the basis of these determinations the appropriate polymorph can be selected for the development of pharmaceutical formulations.

From the great number of such efforts only a few will be mentioned. Thus, Gordon et al. (U.S. Pat. No. 4,476,248) protected a new crystal form of ibuprofen and a process for the preparation thereof; Bunnell et al. (EP 733 635) protected a new crystal form, a process for preparation thereof and a pharmaceutical formulation of the medicament olanzapine containing this new crystal form; R. B. Gandhi et al. (EP 749 969) protected a new process for the preparation of polymorph form I of stavudine from a mixture of one or more forms I, II and III; A. Caron et al. (EP 708 103) protected a new crystal form of irbesartane, a process for the preparation thereof and pharmaceutical formulations containing this crystal form.

It is known [*Acta Cryst.* B34 (1978), 2659–2662 and *Acta Cryst.* B34 (1978), 1304–1310] that torasemide can exist in two crystal modifications differing with regard to the parameters of a single cell, which is confirmed by X-ray diffraction on their monocrystals. Both modifications are formed simultaneously by the slow evaporation of the solvent from a solution of torasemide in a mixture petroleum ether/ethanol. The modification I with melting point 169° C. crystallizes monoclinically in the space group $P\, 2_1/c$ (prisms), while the modification II with melting point 162° C. crystallizes monoclinically in the space group P 2/n (foils). Additionally, for the modification I the melting point 169.22° C. is stated in *Iyakuhin Kenkyu* 25 (1994), 734–750.

According to Example 71 of DE 25 16 025 torasemide in a crystal form with melting point 163–164° C. is obtained.

In U.S. Pat. No. 4,743,693 and U.S. Pat. No. reissue 34,580 or U.S. Pat. No. 4,822,807 and U.S. Pat. No. reissue 34,672 there is disclosed a process for the preparation of a stable modification I of torasemide from an unstable modification II of torasemide by adding a catalytic amount (1%) of a stable modification I of torasemide into a suspension of the unstable modification in water and stirring the mixture at a temperature from room temperature to 90° C. within 3 hours to 14 days. In U.S. Pat. No. 4,743,693 and U.S. Pat. No. reissue 34,580 it is stated that the stable modification I of torasemide (monoclinic, space group $P2_1/c$) has a melting point of 162° C. and the unstable modification II of torasemide (monoclinic, space group P 2/n) has a melting point 169° C., which is contrary to the statements in *Acta Cryst.* B34 (1978), 2659–2662, *Acta Cryst.* B34 (1978), 1304–1310 and *Iyakuhin Kenkyu* 25 (1994), 734–750.

In the abstract of U.S. Pat. No. 4,822,807 the authors ascribe the melting point 162° C. to the stable polymorph I of torasemide and the melting point 169° C. to the unstable polymorph II of torasemide, whereas in the claims of the said patent different melting points for either polymorph are stated, namely for polymorph I the melting point 169° C. and for polymorph II the melting point 162° C.

In the abstract of U.S. Pat. No. reissue 34,672 the authors ascribe the melting point 162° C. to the pure modification I of torasemide and the melting point 169° C. to the modification II of torasemide, whereas in the claims the melting point 159–161.5° C. for the pure polymorph I and the melting point from about 157.5 to about 160° C. for the unstable polymorph II are stated.

SUMMARY OF INVENTION

It has now been surprisingly found that by a controlled acidifying of alkaline solutions of torasemide with inorganic or organic acids with or without addition of a seed crystal at a temperature between 0 and 35° C. within 15 minutes to 25 hours, a new crystal modification III of torasemide can be prepared.

By the alkaline solutions of torasemide according to the process of the present invention there are meant an alkaline extract of the original reaction mixture for the synthesis of torasemide, alkaline solutions of any crystal modification I, II or III of torasemide or alkaline solutions of any mutual mixtures of crystal modifications I, II or III of torasemide.

In the process of the present invention for the preparation of alkaline solutions of torasemide modifications, water solutions of lithium, sodium and potassium hydroxide as well as water solutions of sodium and potassium carbonate can be used.

The acidifying of the alkaline torasemide solutions according to the invention can be performed in inorganic acids such as hydrochloric, sulfuric, phosphoric and nitric acids and in organic acids such as formic, acetic, propionic, oxalic, tartaric, methanesulfonic and p-toluenesulfonic acids.

As the seed crystal in the processes of the present invention crystal powder of one of the isostructure substances, particularly crystal powder of the crystal modification III of torasemide can be used.

It has additionally been found that by using the process of the present invention no decomposition of torasemide occurs and the impurities that may be present in the alkaline extract of the original reaction mixture for the synthesis of torasemide or in modifications I, II or III of torasemide pass, by the present process, into bases, i.e. a chemically pure crystal modification III of torasemide is obtained.

Moreover, it has been found that the new crystal modification III of torasemide is stable under normal storage conditions as well as at being subjected to increased humidity, which means that it is neither transformed into the unstable modification II of torasemide nor into the stable modification I of torasemide.

The new crystal modification III of torasemide has a characteristic X-ray powder pattern obtained by X-ray diffraction on a powder sample of the new crystal modification III of torasemide in the instrument PHILIPS PW3710 under Cu X-rays [$\lambda(CuK\alpha_1)$=1.54046 Å and $\lambda(CuK\alpha_2)$=1.54439 Å]. Thus obtained characteristic spacings between lattice planes designated by >>d<< and expressed in Angström units and their corresponding characteristic relative intensities designated by >>$I/I_0$<< and expressed in % are represented in Table 1.

TABLE 1

| Modification III | |
|---|---|
| d(Å) | $I/I_0$(%) |
| 15.3898 | 2.8 |
| 12.5973 | 5.4 |
| 11.4565 | 5.8 |
| 9.7973 | 69.8 |

TABLE 1-continued

| Modification III | |
|---|---|
| d(Å) | $I/I_0$(%) |
| 9.5493 | 76.6 |
| 8.6802 | 28.5 |
| 8.2371 | 100.0 |
| 7.6351 | 10.2 |
| 7.3356 | 13.0 |
| 6.9759 | 1.2 |
| 6.5351 | 10.0 |
| 6.3240 | 7.9 |
| 6.1985 | 4.5 |
| 5.9521 | 0.6 |
| 5.6237 | 24.4 |
| 5.5623 | 29.7 |
| 5.4040 | 19.6 |
| 5.1119 | 10.3 |
| 4.8738 | 22.7 |
| 4.7865 | 46.9 |
| 4.6986 | 45.7 |
| 4.5985 | 17.9 |
| 4.4602 | 24.7 |
| 4.3405 | 90.0 |
| 4.2552 | 20.7 |
| 4.1829 | 19.9 |
| 4.0768 | 19.9 |
| 3.9377 | 47.1 |
| 3.8659 | 29.3 |
| 3.8429 | 35.3 |
| 3.7801 | 42.8 |
| 3.7248 | 11.9 |
| 3.6239 | 31.7 |
| 3.5556 | 20.5 |
| 3.4825 | 7.8 |
| 3.4130 | 8.1 |
| 3.3055 | 15.5 |
| 3.2298 | 8.2 |
| 3.1786 | 10.7 |
| 3.1278 | 5.6 |
| 3.0699 | 7.1 |
| 3.0078 | 17.5 |
| 2.9549 | 5.1 |
| 2.9056 | 4.3 |
| 2.8541 | 1.8 |
| 2.7686 | 13.9 |
| 2.6988 | 5.7 |
| 2.6610 | 6.3 |
| 2.6293 | 7.3 |
| 2.5549 | 3.7 |
| 2.5236 | 2.0 |
| 2.4485 | 5.3 |
| 2.4161 | 6.7 |
| 2.3671 | 2.0 |
| 2.3133 | 3.6 |
| 2.2788 | 7.6 |
| 2.2312 | 3.4 |
| 2.1852 | 6.2 |
| 2.1468 | 3.0 |
| 2.0957 | 4.7 |
| 2.0617 | 4.1 |
| 2.0273 | 3.3 |
| 1.9896 | 3.1 |
| 1.9688 | 4.1 |
| 1.9274 | 2.6 |
| 1.8853 | 2.7 |
| 1.7931 | 2.1 |
| 1.7449 | 1.0 |
| 1.7169 | 1.8 |
| 1.6512 | 1.0 |
| 1.6122 | 0.8 |
| 1.5601 | 0.8 |
| 1.5320 | 0.3 |
| 1.5057 | 0.5 |
| 1.4521 | 0.3 |
| 1.3773 | 0.6 |

In addition, by recording the monocrystal of the new crystal modification III of torasemide in four circle PHILIPS PW 1100/Stoe&Cie diffractometer under Mo X-rays [λ(MoKα)=0.71073 Å] there were obtained the basic crystallographic data for a single cell, which show in comparison with the literature data for crystal modifications I and II of torasemide [*Acta Cryst.* B34 (1978), 2659–2662 and *Acta Cryst.* B34 (1978), 1304–1310] that this is an absolutely new crystal modification III of torasemide.

The basic crystallographic data (diffraction on monocrystal) for modifications I, II and the new crystal modification III of torasemide are represented in Table 2.

TABLE 2

| | Crystal modification of torasemide | | |
|---|---|---|---|
| Parameter | I | II | III |
| crystal composition | monoclinic | monoclinic | monoclinic |
| space group | P $2_1$/c | P 2/n | P $2_1$/c |
| a (Å) | 13.308 | 20.446 | 11.430 |
| b (Å) | 8.223 | 11.615 | 19.090 |
| c (Å) | 31.970 | 16.877 | 16.695 |
| β (°) | 107.01 | 108.90 | 93.903 |
| V (Å$^3$) | 3345.5 | 3791.9 | 3634.7 |
| Z | 4 × 2 | 4 × 2 | 4 × 2 |

The new crystal modification III of torasemide prepared according to the process of the present invention can be transformed by the use of common processes to the crystal modification I of torasemide, i.e. it can be used as a starting material for the preparation of known crystal modification I of torasemide.

The new crystal modification III of torasemide prepared according to the invention can be transformed to pharmaceutically acceptable salts of torasemide by the use of common processes.

The dissolution profile (USP 23) of the new crystal modification III of torasemide in water and in artificial intestinal juice in comparison to dissolution profiles of known crystal modifications I and II of torasemide, in the same fluids, shows a significant difference.

IDR (Intrinsic Dissolution Rate) of the new crystal modification III of torasemide in a model of artifical gastric juice exceeds 1 mg cm$^{-2}$ min$^{-1}$, which indicates a potential good bioavailability.

The new crystal modification III of torasemide is prepared according to the process of the present invention in the form of a flowable crystal powder of a prismatic habitus, which exhibits flowability, i.e. it comes in a "free flow" form, wherein no static charge accumulation occurs.

The new crystal modification III of torasemide prepared according to the process of the present invention can be used as a suitable torasemide form as a diuretic as well as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, for decreasing intraocular pressure, acute or chronic bronchitis, in the treatment of cerebral edema caused by trauma, ischemia, concussion of the brain, metastases or epileptic attacks and in the treatment of nasal infections caused by allergens.

The present invention also relates to pharmaceutical forms such as tablets containing the new crystal modification III of torasemide as the active ingredient combined with one or more pharmaceutically acceptable additives such as sugar, starch, starch derivatives, cellulose, cellulose derivatives, mould release agents, and antiadhesive agents and possibly agents for flowability regulation. When using the new crystal modification III of torasemide for the preparation of pharmaceutical forms, also process steps taking place in water, e.g. granulation, can be used.

The starting materials for the process of the present invention i.e. the alkaline extract of the original reaction mixture for torasemide synthesis can be prepared according to DE 25 16 025, whereas the modifications I and II of torasemide can be prepared according to *Acta Cryst.* B34 (1978), 1304–1310.

BEST AND VARIOUS MODES FOR CARRYING OUT INVENTION

Figure 1:
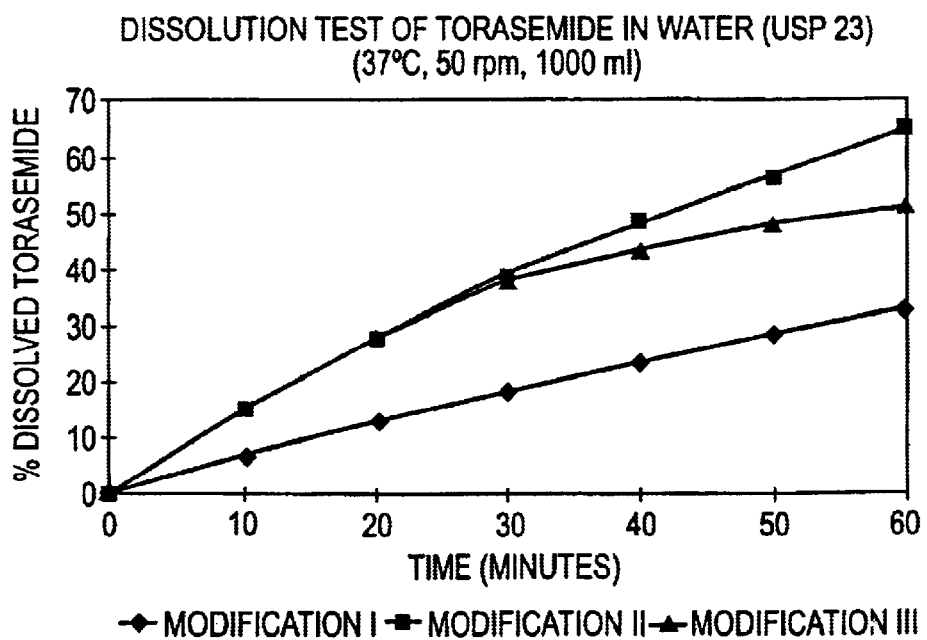
FIG. 1 is a graph of dissolution tests of torasemide in water.

The present invention is illustrated but in no way limited by the following Examples.

EXAMPLE 1

Technically Pure New Crystal Modification III of Torasemide:

The original alkaline extract of the reaction mixture for torasemide synthesis (1000 ml) prepared according to DE 25 16 025 was acidified with 10% aqueous acetic acid solution under the addition of 1.4 g of a crystal modification III of torasemide. The suspension was stirred at room temperature for 90 minutes. The crystals were sucked off, washed with 1 liter of demineralized water and dried in a vacuum dryer at 50° C. for 3 hours. There were obtained 125 g of a crystal modification III of torasemide, m.p. 162–165° C.

The X-ray powder pattern of the thus obtained sample corresponded to the new crystal modification III of torasemide. The content of torasemide according to the HPLC method was >99%.

EXAMPLE 2

The crystal modification III of torasemide (1000 g) prepared according to the Example 1 was dissolved in a 10-fold amount of 5% aqueous potassium hydroxide solution and at the temperature of 20° C. the obtained solution was acidified with 5% aqueous hydrochloric acid solution under the addition of 10 g of a crystal modification III of torasemide. The suspension was stirred at 20° C. for 120 minutes. The crystals were sucked off, washed with 4 liters of demineralized water and dried in a vacuum dryer at 50° C. for 3 hours. There were obtained 961 g of a modification III of torasemide, m.p. 165° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 3

The crystal modification I of torasemide (1.00 g) prepared according to *Acta Cryst.* B34 (1978), 1304–1310 was dissolved in a 10-fold amount of 10% aqueous sodium carbonate solution and at the temperature of 15° C. the obtained solution was acidified with 5% aqueous sulfuric acid solution under the addition of 0.10 g of the modification III of torasemide. The suspension was stirred at 15° C for 120 minutes. The crystals were sucked off, washed with 4 ml of demineralized water and dried in a vacuum dryer at 50° C. for 3 hours. There were obtained 0.95 g of a crystal modification III of torasemide, m.p. 165–166° C.

The X-ray powder pattern of the thus obtained sample corresponded to the crystal modification III of torasemide. The content of torasemide according to the HPLC method was >995%, i.e. it corresponded to chemically pure torasemide.

EXAMPLE 4

The crystal modification II of torasemide (1.00 g) prepared according to *Acta Cryst.* B34 (1978), 1304–1310 was dissolved in a 10-fold amount of 10% aqueous potassium carbonate solution and then at the temperature of 15° C. the obtained solution was acidified with 5% aqueous nitric acid solution under the addition of 0.10 g of a modification III of torasemide. The suspension was stirred at 15° C. for 120 minutes. The crystals were sucked off, washed with 4 ml of demineralized water and dried in a vacuum dryer at 50° C. for 3 hours. There were obtained 0.96 g of a crystal modification III of torasemide, m.p. 164–166° C.

The X-ray powder pattern of the thus obtained sample corresponded to the crystal modification III of torasemide. The content of torasemide according to the HPLC method was >99,5%, i.e. it corresponded to chemically pure torasemide.

EXAMPLE 5

A mixture of crystal modifications I and II of torasemide (1.00 g) prepared according to *Acta Cryst.* B34 (1978), 1304–1310 was dissolved in a 10-fold amount of 10% aqueous lithium hydroxide solution and then at room temperature the obtained solution was acidified with 5% aqueous phosphoric acid solution under the addition of 0.10 g of a modification III of torasemide. The suspension was stirred at 15° C. for 240 minutes. The crystals were sucked off, washed with 4 ml of demineralized water and dried in a vacuum dryer at 50° C. for 3 hours. There were obtained 0.97 g of a crystal modification III of torasemide, m.p. 165–166° C.

The X-ray powder pattern of the thus obtained sample corresponded to the crystal modification III of torasemide. The content of torasemide according to the HPLC method was >99,5%, i.e. it corresponded to chemically pure torasemide.

EXAMPLE 6

A mixture of crystal modifications I and III of torasemide (1.00 g) prepared according to *Acta Cryst.* B34 (1978), 1304–1310 and Example 1 was dissolved in a 10-fold amount of 5% aqueous potassium hydroxide solution and then at the temperature of 30° C. the obtained solution was acidified with 10 % aqueous tartaric acid solution under the addition of 0.10 g of a modification III of torasemide. The suspension was stirred at 30° C. for 180 minutes. The crystals were sucked off, washed with 4 ml of demineralized water and dried in a vacuum dryer at 50° C. for 3 hours. There were obtained 0.93 g of a crystal modification III of torasemide, m.p. 164–166° C. The X-ray powder pattern of the thus obtained sample corresponded to the crystal modification III of torasemide. The content of torasemide according to the HPLC method was >99,5%, i.e. it corresponded to chemically pure torasemide.

EXAMPLE 7

A mixture of crystal modifications II and III of torasemide (1.00 g) prepared according to *Acta Cryst.* B34 (1978), 1304–1310 and Example 1 was dissolved in a 10-fold amount of 5% aqueous sodium hydroxide solution and then at the temperature of 35° C. the obtained solution was acidified with 5% aqueous propionic acid solution under the addition of 0.10 g of a modification III of torasemide. The suspension was stirred at 35° C. for 90 minutes. The crystals were sucked off, washed with 4 ml of demineralized water and dried in a vacuum dryer at 50° C. for 3 hours. There were obtained 0.87 g of a crystal modification III of torasemide, m.p. 165° C.

The X-ray powder pattern of the thus obtained sample corresponded to the crystal modification III of torasemide. The content of torasemide according to the HPLC method was >99,5%, i.e. it corresponded to chemically pure torasemide.

EXAMPLE 8

A mixture of crystal modifications I, II and III of torasemide (1.00 g) prepared according to *Acta Cryst.* B34 (1978), 1304–1310 and Example 1 was dissolved in a 10-fold amount of 10% aqueous sodium carbonate solution and then at the temperature of 25° C. the obtained solution was acidified with 5% aqueous p-toluenesulfonic acid solution under the addition of 0.10 g of a modification III of torasemide. The suspension was stirred at 25° C. for 60 minutes. The crystals were sucked off, washed with 4 ml of demineralized water and dried in a vacuum dryer at 50° C. for 3 hours. There were obtained 0.93 g of a crystal modification III of torasemide, m.p. 164–166° C.

The X-ray powder pattern of the thus obtained sample corresponded to the crystal modification III of torasemide. The content of torasemide according to the HPLC method was >99,5%, i.e. it corresponded to chemically pure torasemide.

EXAMPLE 9

A crystal modification I of torasemide (1.00 g) prepared according to *Acta Cryst.* B34 (1978), 1304–1310 was dissolved in a 10-fold amount of 10% aqueous potassium carbonate solution and then at the temperature of 15° C. the obtained solution was stepwise acidified with 10% aqueous acetic acid solution under the simultaneous stepwise lowering of the temperature of the mixture to 0° C. At this temperature the suspension was stirred for 25 hours. The crystals were sucked off, washed with 4 ml of demineralized water and dried in a vacuum dryer at 50° C. for 3 hours. There were obtained 0.94 g of a crystal modification III of torasemide, m.p. 164–166° C.

The X-ray powder pattern of the thus obtained sample corresponded to the crystal modification III of torasemide. The content of torasemide according to the HPLC method was >99,5%, i.e. it corresponded to chemically pure torasemide.

EXAMPLE 10

Production of 2.5 mg Tablets

Torasemide of the crystal modification III was mixed with lactose and corn starch in a common manner, granulated with water, dried and sieved (granulate 1). Colloidal silicon dioxide and magnesium stearate were mixed, sieved and admixed into granulate 1. This mixture was then tabletized in a common manner. For the production of 100 000 tablets the following is required:

| | |
|---|---|
| torasemide-crystal modification III | 0.25 kg |
| lactose (Lactose Extra Fine Crystal HMS ®) | 6.05 kg |
| corn starch (Starch ®) | 1.60 kg |
| colloidal silicon dioxide (Aerosil 200 ®) | 60.00 g |
| magnesium stearate | 40.00 g |
| redistilled water | 1.20 kg |

EXAMPLE 11

Production of 100 mg Tablets

Torasemide of crystal modification III was mixed with lactose and corn starch and a part of magnesium stearate in a common manner. The mixture was compressed and sieved to obtain the desired grain size and distribution of grain size (granulate 1). Colloidal silicon dioxide and magnesium stearate were mixed, sieved and admixed into granulate 1. This mixture was then tabletized in a common manner. For the production of 100 000 tablets the following is required:

| | |
|---|---|
| torasemide-crystal modification III | 10.0 kg |
| lactose (Lactose Extra Fine Crystal HMS ® | 2.0 kg |
| corn starch (Starch ®) | 7.7 kg |
| colloidal silicon dioxide (Aerosil 200 ®) | 0.2 kg |
| magnesium stearate | 0.1 kg |

EXAMPLE 12

The microcrystallinic modifications I, II and III of torasemide prepared according to *Acta Crst.* B34 (1978), 1304–1310 and Example I were subjected to dissolution testing in water, and in artificial Intestinal juice, at 37° C. (USP 23), and results are reported in tables 3 and 4.

TABLE 3

Dissolution test of torasemide in water (USP 23)
(37° C., 50 rpm., 1000 ml)

| | % Dissolved torasemide | | |
|---|---|---|---|
| Minutes | Mod. I | Mod. II | Mod. III |
| 0 | 0 | 0 | 0 |
| 10 | 6.7 | 15.1 | 15.6 |
| 20 | 13.0 | 27.8 | 28.1 |
| 30 | 18.5 | 39.2 | 37.7 |
| 40 | 23.5 | 48.8 | 43.6 |
| 50 | 28.5 | 56.3 | 48.5 |
| 60 | 32.8 | 65.1 | 51.1 |

TABLE 4

Dissolution test of torasemide in artificial
intestinal juice (USP 23)
(37° C., 50 rpm, pH 7.5, 1000 ml)

| | % Dissolved torasemide | | |
|---|---|---|---|
| Minutes | Mod. I | Mod. II | Mod. III |
| 0 | 0 | 0 | 0 |
| 10 | 29.4 | 73.3 | 41.0 |
| 20 | 40.5 | 92.6 | 59.8 |
| 30 | 48.4 | 95.5 | 70.2 |
| 40 | 54.2 | 96.8 | 77.6 |
| 50 | 59.2 | 96.3 | 82.5 |
| 60 | 65.0 | 98.2 | 88.7 |

Figure 2:
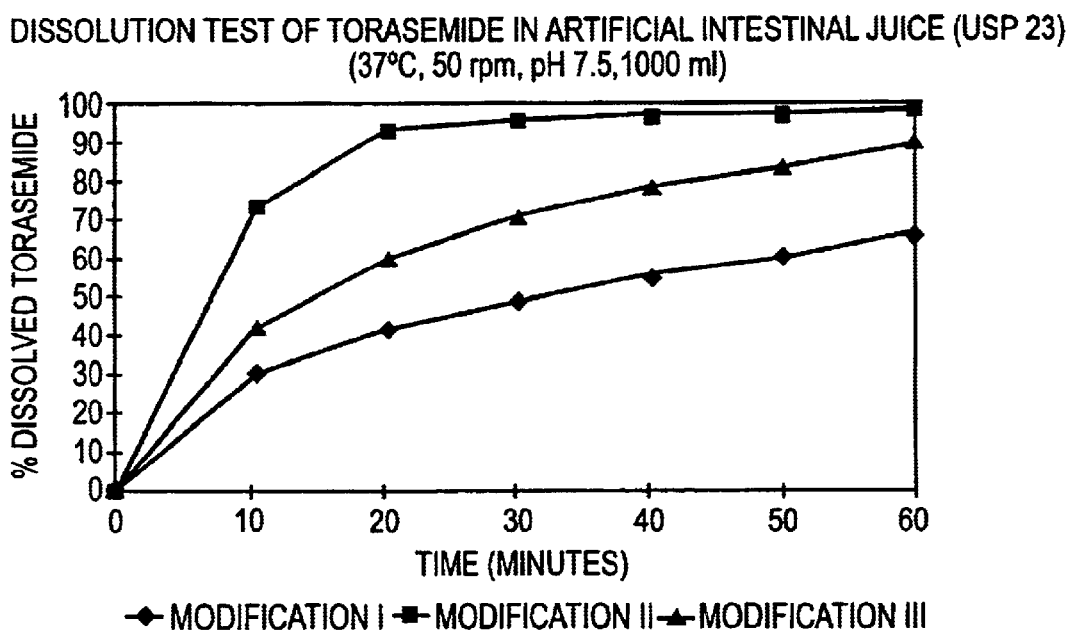
FIG. 2 is a graph of dissolution tests of torasemide in artificial intestinal juice.

The results reported in Table 3 were plotted in the FIG. 1. The results reported in Table 4 were plotted in the FIG. 2.

What is claimed is:

1. Pure polymorphic crystal modification III of torasemide, wherein the purity is greater than 99%.

2. The polymorphic crystal modification of claim 1 wherein the purity is greater than 99.5%.

3. Pure polymorphic crystal modification III of torasemide which is stable under normal storage conditions.

4. Pure polymorphic crystal modification III of torasemide which is stable under increased humidity.

5. Pure polymorphic crystal modification III of torasemide produced by a process comprising the controlled acidifying of an alkaline torasemide solution with an inorganic or organic acid at a temperature between 0° to 35° C. for 15 minutes to 25 hours.

6. The pure polymorphic crystal modification III of torasemide according to claim 5, wherein the alkaline torasemide solution is an alkaline extract of an original reaction mixture for the synthesis of torasemide.

7. The pure polymorphic crystal modification III of torasemide according to claim 5, wherein the alkaline torasemide solution is an alkaline solution of any crystal modification I, II, or III of torasemide or an alkaline solution of any mutual mixture of crystal modifications I, II, or III of torasemide.

8. The pure polymorphic crystal modification III of torasemide according to claim 5, wherein a water solution of lithium, sodium, or potassium hydroxide or a water solution of sodium or potassium carbonate is used for the preparation of the alkaline torasemide solution.

9. The pure polymorphic crystal modification III of torasemide according to claim 5, wherein an inorganic acid is used for acidifying.

10. The pure polymorphic crystal modification III of torasemide according to claim 5, wherein the inorganic acid is selected from the group consisting of hydrochloric, sulfuric, phosphoric, and nitric acid.

11. The pure polymorphic crystal modification III of torasemide according to claim 5, in which the organic acid is formic, acetic, propionic, oxalic, tartaric, methanesulfonic, or p-toluenesulfonic acid.

12. The pure polymorphic crystal modification III of torasemide according to claim 5, wherein a seed crystal is added in the controlled acidifying.

13. The pure polymorphic crystal modification III of torasemide according to claim 12, wherein the seed crystal is crystal powder of one of the isocrystallinic substances of torasemide.

14. The pure polymorphic crystal modification III of torasemide according to claim 13, wherein the seed crystal is crystal powder of crystal modification III of torasemide.

15. The pure polymorphic crystal modification III of torasemide according to claim 5, wherein no seed crystal is added in the controlled acidifying.

16. A pharmaceutical composition according to claim 1, which comprises as an active ingredient the pure polymorphic crystal modification III of torasemide combined with one or more pharmaceutically acceptable carriers, additives, or diluents.

17. The pharmaceutical composition according to claim 16, wherein the composition in tablet form.

18. The pure polymorphic crystal modification III of torasemid according to claim 5, wherein an organic acids is used for acidfying.

19. The pharmaceutical composition according to claim 16, wherein the composition is a tablet.

20. The pharmaceutical composition according to claim 16, wherein the crystal modification is stable under normal stage conditions.

21. The pharmaceutical composition according to claim 16, wherein the crystal modification is stable under increased humidity.

22. A pharmaceutical composition stable under normal storage conditions and under increased humidity comprising a torasemide polymorphic crystal modification having the following crystallographic characteristics:

| Parameter | Crystal modification of torasemide |
| --- | --- |
| crystal composition | monoclinic |
| spacegroup | $P2_1/c$ |
| a (Å) | 11.430 |
| b (Å) | 19.090 |
| c (Å) | 16.695 |
| β (°) | 93.903 |
| V (Å$^3$) | 3634.7 |
| Z | 4 × 2. |

23. A pharmaceutical composition according to claim 22, wherein the torasemide polymorphic crystal modification purity is greater than 99%.

24. A pharmaceutical composition according to claim 22 further comprising one or more pharmaceutically acceptable carriers, additives, or diluents.

25. The pharmaceutical composition according to claim 24, wherein the crystal modification is prepared in the form of a crystal powder which is in a free flow form wherein no static charge accumulation occurs.

26. A pharmaceutical composition according to claim 24, wherein the purity of the polymorphic crystal modification of torasemide is greater than 99%.

27. A pharmaceutical composition according to claim 24, wherein the composition is in tablet form.

* * * * *

UNITED STATES PATENT AND TRADEMARK OFFICE
CERTIFICATE OF CORRECTION

PATENT NO. : 6,833,379 B2
DATED : December 21, 2004
INVENTOR(S) : Darko Filić et al.

It is certified that error appears in the above-identified patent and that said Letters Patent is hereby corrected as shown below:

Title page,
Item [12], "Filićet al." should read -- Filić et al. --.

Column 11,
Line 14, "composition in" should read -- composition is in.
Line 16, "acids" should read -- acid --.
Lines 18-19, delete the claim in its entirety and insert therefore -- The pharmaceutical composition according to claim 16, wherein the crystal modification is in the form of a crystal powder which is in a free flow form wherein no static charge accumulation occurs. --.

Signed and Sealed this

Fifth Day of April, 2005

JON W. DUDAS
*Director of the United States Patent and Trademark Office*